United States Patent [19]
Aho et al.

[11] Patent Number: 4,874,228
[45] Date of Patent: Oct. 17, 1989

[54] BACK-LIT DISPLAY

[75] Inventors: Kenneth A. Aho, Chisago City; Jeffrey J. Melby, St. Paul; Richard A. Miller, Stillwater, all of Minn.

[73] Assignee: Minnesota Mining and Manufacturing Company, St. Paul, Minn.

[21] Appl. No.: 292,762

[22] Filed: Jan. 3, 1989

Related U.S. Application Data

[63] Continuation-in-part of Ser. No. 30,033, Mar. 24, 1987, Pat. No. 4,799,137.

[51] Int. Cl.⁴ ............................ G02F 1/133; G02F 1/01
[52] U.S. Cl. ....................................... 350/345; 362/23; 362/26; 362/309; 362/327; 362/339
[58] Field of Search ................ 362/299, 301, 303, 304, 362/309, 327, 347, 348, 349, 339, 31, 255, 256, 23, 26, 29; 350/338, 339 D, 345

[56] References Cited

U.S. PATENT DOCUMENTS

| | | | |
|---|---|---|---|
| 4,011,001 | 3/1977 | Moriya | 350/345 |
| 4,215,647 | 8/1980 | Fukasawa | 362/29 |
| 4,266,859 | 5/1981 | Jogashi | 350/338 |
| 4,298,249 | 11/1981 | Gloor et al. | 350/338 |
| 4,340,277 | 7/1982 | Kaufmann et al. | 350/338 |
| 4,799,137 | 1/1989 | Aho | 362/339 |

FOREIGN PATENT DOCUMENTS

| | | | |
|---|---|---|---|
| 2511252 | 9/1975 | Fed. Rep. of Germany | 362/26 |
| 2536504 | 5/1984 | France | 362/26 |

Primary Examiner—Ira S. Lazarus
Assistant Examiner—Sue Hagarman
Attorney, Agent, or Firm—Donald M. Sell; Walter N. Kirn; Stephen Buckingham

[57] ABSTRACT

A back-lit display utilizes a light transmissive film having a smooth surface and a structured surface. The structured surface has a series of triangular prisms running parallel or concentric to one another. A reflector is placed adjacent to the smooth surface so that light entering the film at an angle that is close to parallel to the smooth surface will emerge from the film at a predetermined angle with respect to the incoming beam. A display, that could be a liquid crystal display, is positioned so that light reflected by the film passes through it.

18 Claims, 3 Drawing Sheets

BACK-LIT DISPLAY

RELATED APPLICATIONS

This is a continuation-in-part of application Ser. No. 030,033 filed Mar. 24, 1987, now U.S. Pat. No. 4,799,137.

FIELD OF THE INVENTION

The present invention relates to optical films and more particularly to back-lit displays utilizing an optical film that will reflect light at a predetermined constant angle relative to the angle of incidence.

BACKGROUND OF THE INVENTION

In many situations a light source is desired to provide a collimated beam of light. The typical method of providing such a collimated beam of light is to utilize a parabolic reflector. Two disadvantages exist in the use of parabolic reflectors, however. One disadvantage relates to the size of a parabolic reflector. If the light source is to have a large aperture, a parabolic reflector must be relatively deep, and thus enclose a large volume. This is particularly true if the parabolic reflector has a relatively short focal length. In situations where space is limited, such as automobile taillights or back-lit displays, the size of such reflectors can be a significant disadvantage.

A second disadvantage lies in the existence of "hot" spots in the light pattern produced by a parabolic reflector. Such hot spots arise from the fact that the parabolic reflector is more efficient at gathering light near the center than at the edges. A parabolic reflector, thus, is not optimum for use in a light source where a uniform intensity is desired.

One alternative to the use of a parabolic reflector is shown in U.S. Pat. No. 4,789,921, commonly assigned herewith. In the approach shown in that application a reflector has Fresnel structures that cause the reflector to have the properties of a parabolic reflector when it is formed into the shape of a cone. That approach allows a reflector to be less deep than the equivalent conventional parabolic reflector, but does not solve the problem of providing a uniform intensity over the entire light source.

SUMMARY OF THE INVENTION

A back-lit display according to the invention has a housing defining an optical cavity having an optical window. Inside the optical cavity is a light reflecting film having a structured surface and a smooth surface. The structured surface has thereon a plurality of triangular prisms. A light reflecting means is adjacent said smooth surface. A light source is positioned to emit light such that the light will enter the film in a direction that is almost parallel to the smooth surface. The actual display means is positioned in the optical window.

DETAILED DESCRIPTION OF THE PREFERRED EMBODIMENTS

Figure 1:
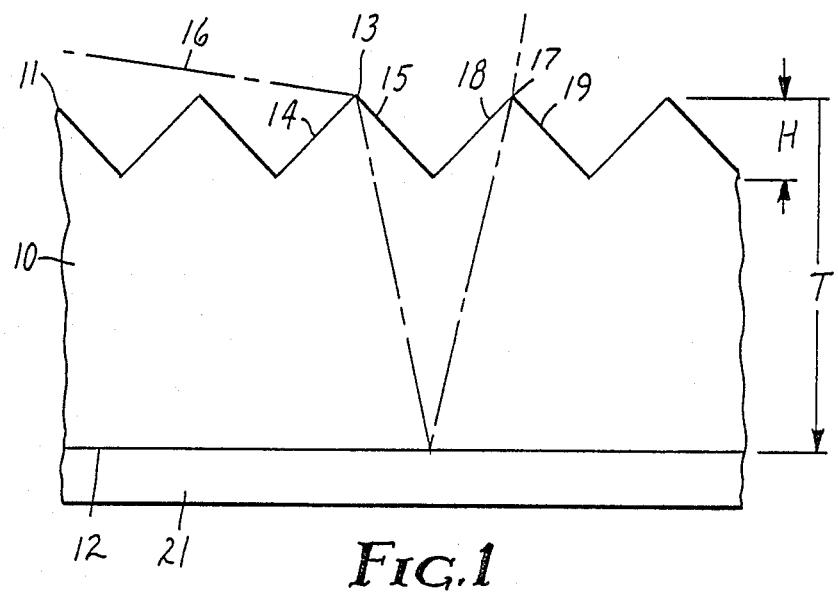
FIG. 1 is a schematic view of a film used in the invention and a light ray entering the film near the top of one of the triangular prisms.

FIG. 1 shows a transparent film having a structured surface 11 and a smooth surface 12. Smooth surface 12 is equipped with a light reflective means 21. In the preferred embodiment reflector 21 is a vacuum deposited layer of aluminum.

Structured surface 11 has a plurality of triangular prisms such as prism 13. Prism 13 has sides 14 and 15. In the preferred embodiment, sides 14 and 15 meet at a right angle and, if projected to surface 12, would meet that surface at 45° angles. Thus, in the preferred embodiment the cross sections of the prisms form right isosceles triangles, with the right angles forming peaks and the legs forming a series of grooves, although other angles may be chosen and will provide reflections of other angles.

Prism 13 and others like it, each have a major axis which runs parallel to the peak of the prism. The axes of all the prisms on the film run parallel to one another.

Light beam 16 enters film 10 through facet 14 of prism 13 near the intersection of facets 14 and 15. Light beam 16 is refracted and then totally internally reflected off facet 15 of prism 13. After total internal reflection light beam 16 passes through film 10 and is reflected off reflector 21. It then passes through film 10 in the other direction and emerges through facet 19 of prism 17. At that time it is refracted a second time and emerges in a direction substantially perpendicular to incoming beam 16.

Figure 2:
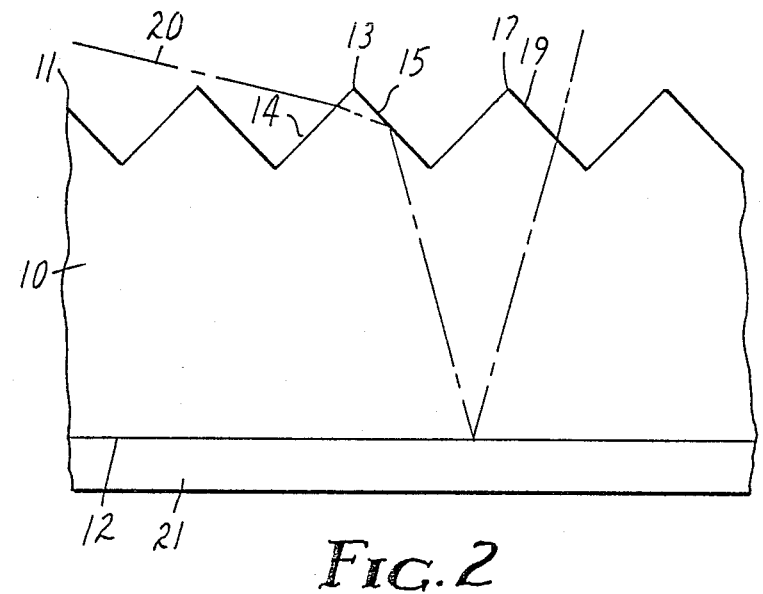
FIG. 2 is a schematic view of a film used in the invention with a light ray entering towards the center of one of the triangular prisms.

FIG. 2 shows light ray 20 entering through facet 14 of prism 13 in a location more distant from the intersection of facets 14 and 15 than was the case with light ray 16 of FIG. 1. Light ray 20 is refracted upon passing through facet 14 and is totally internally reflected by facet 15. It is then reflected by reflector 21 and emerges through facet 19 of prism 17. As with light ray 16, light ray 20 is refracted upon emerging from film 10 and emerges in a direction substantially perpendicular to incoming light ray 20.

An important feature of the invention, as illustrated in FIGS. 1 and 2, relates to the fact that the outgoing light beam always emerges at a predetermined angle relative to the incoming beam. Thus, film 10 may be rotated around an axis running parallel to the axes of the prisms without affecting the direction of the outgoing light beam.

Returning to FIG. 1 the height of the prisms is designated H and the thickness of the film, i.e., the distance from surface 12 to the peaks of the prisms is designated T. In the preferred embodiment, where the light is intended to emerge in a direction perpendicular to the incoming light beam, performance has been determined to be optimized when the light beam emerges through the prism adjacent to the one through which it enters. This is accomplished when T is equal to 3.2152H. Thus if H is equal to 0.007 inches, T should be 0.225 inches. In spite of the fact that this ratio would provide optimum performance, however, films according to the invention have been found to perform adequately when deviating from this ratio.

If the direction of the incoming ray of light deviates by too great an extent from parallel to surface 12, the efficiency of the reflector will be reduced because some of the light will not strike the reflecting facet of the prism through which it enters. Assuming that the index of refraction of the film is 1.495, the index of the films used in testing the reflective films used in the invention, the maximum angle that the incoming light ray should make with surface 12 is 13.1°, although angles of as much as 20° have produced adequate and acceptable results. Even greater angles may be used if decreased efficiencies can be tolerated in a given application.

If the angle between the incoming light and surface 12 becomes too small, efficiency will again be reduced because most of the light will enter near the peaks of the prism where small deviations from sharpness are very important. Furthermore, small deviations in the height of the prisms become more important at narrow entry angles. For this reason, angles less than 1° are not generally recommended, although theoretically possible.

As described, the film of the invention has right isosceles prisms, the sides of which each form a 45° angle with the smooth surface. The invention does not require such prisms, however. The prisms may have included angles of sizes other than 90° and need not be isosceles. If an isosceles triangle with an included angle of less than 90° is used, the film will perform similarly to the one described, but the reflected beam will emerge at an angle of less than 90°. Conversely, isosceles prisms with included angles of greater than 90° will cause the reflected beam to emerge at an angle of greater than 90° with respect to the incoming beam.

Figure 3:
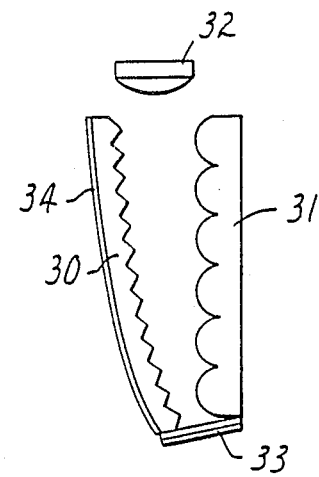
FIG. 3 is a schematic view of a lighting element utilizing the film used in the invention.

FIG. 3 shows a light fixture utilizing the film of the present invention. The light fixture includes right angle reflecting film 30 with a reflector 34, a lens 31, and light source 32. Light source 32 directs a substantially collimated light at film 30 from angle that will be within the range of angles where film 30 provides its most efficient right angle reflection. Lens 31 may be any type of lens conventionally used with light fixtures. For example, if the light fixture of FIG. 3 were to be used in an automobile taillight, lens 31 could be a conventional pillow lens which will spread the emitted light to meet established safety standards. In other types of light fixtures, other appropriate lenses may be selected. As may be seen in FIG. 3, right angle reflector film 30 is set an angle to lens 31. This is done so that the light from light source 32 can strike right angle reflector film 30 at an angle of greater than one degree and be reflected perpendicularly to lens 31.

A light fixture of the type shown in FIG. 3 will be much more compact than the conventional light fixtures utilizing conventional parabolic reflectors. This is because the light fixture of FIG. 3 need only be wide enough to accommodate light source 32. Light source 32 may also be made very compact. This is because there is no requirement that it have a large aperture like the light fixture itself. Therefore, light source 32 may utilize a compact reflector, thereby occupying little space itself. If required, more than one light source may be used.

In the preferred embodiment right angle reflecting film 30 is curved as shown in FIG. 3. This is because parabolic light sources such as light source 32 typically do not provide perfectly collimated light. Thus, the flux density of light received by right angle reflector film 30 would vary along the length, with the portion of right angle reflector film 30 which is more distant from light source 32 receiving less light, if right angle reflector 30 were flat. By providing the curvature shown, all portions of right angle reflector film 30 will receive equal flux densities and thus the light fixture will provide more uniform illumination, than would be provided if right angle reflector film 30 were flat. The exact shape of the curve will, of course, depend on the nature of light source 32. If desired, reflecting film 30 could be curved in such a manner that the resulting light fixture would appear brighter on the end more distant from light source 32.

The efficiency of the light source of FIG. 3 may be improved by including a reflector 33 at the end of the light fixture opposite light source 32. This mirror will reflect light that is emitted by light source 32 but does not strike film 30 back into film 30.

Figure 4:
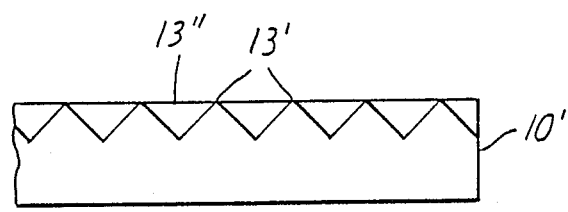
FIG. 4 is a schematic view of an alternative embodiment of the film used in the invention utilizing a round format.

FIG. 4 illustrates an alternative embodiment of the film used in the invention. In the embodiment of FIG. 4 a film 10' has a series of prisms such as prism 13'. Rather than being disposed linearly, as in the previously described embodiments, the prisms of FIG. 4 are circular and concentric. This is shown schematically by the way prism 13' curves into the location shown as 13". A light source may be located at the center of curvature of the concentric prisms. Such a light source should be directed in such a manner as to cause light to strike the film at an angle within the range of angles for which the film provides high efficiency right angle reflection.

Uniform lighting intensity is particularly important for back-lit display panels. An important type of such display panels are liquid crystal displays (LCDs). LCDs are currently being used as flat panel televisions, automotive instrument panels and low power consumption computer displays. In order to maximize both the esthetic appeal and the readability of such displays uniform illumination is critical.

Figure 5:
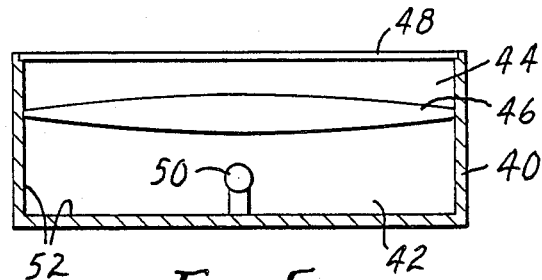
FIG. 5 is a schematic view of a prior art back-lit display.

Various schemes have been utilized in the prior art to provide greater uniformity of illumination in a back-lit display. One such scheme is shown in FIG. 5. In the prior art back-lit display of FIG. 5 a housing 40 defines an optical cavity 42. Optical cavity 42 has an optical window 44. In optical window 44 is a diffuser 46 and a display 48. Inside optical cavity 42 is a light source 50. Typically the interior walls 52 of housing 40 would be reflectorized. As may be seen from FIG. 5, diffuser 46 is tapered so that it is thicker adjacent light source 50 than it is at its edges. Since diffuser 46 is thicker close to light source 50, more of the light in that region is absorbed than is absorbed at the edges. The result is a more uniform level of illumination through display 48.

There are two disadvantages to the use of the tapered diffuser of FIG. 5. The first disadvantage is the difficulty of fabrication of such a tapered diffuser. The second disadvantage is that, since the uniformity of illumination is achieved by absorbing more of the light in some regions, a greater total amount of light must be supplied to achieve the desired brightness level.

Figure 6:
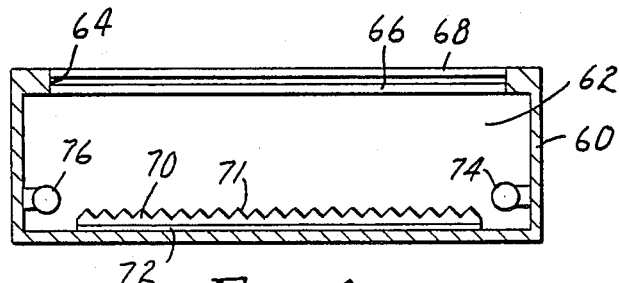
FIG. 6 is a schematic view of a first back-lit display according to the invention.

FIG. 6 shows a back-lit display according to the invention. The embodiment of FIG. 6 includes a housing 60 defining an optical cavity 62. Optical cavity 62 has an optical window 64. In optical window 64 are a diffuser 66 and a display 68. Inside optical cavity 62 are right angle film 70 having structured surface 71 and reflectorized surface 72 and light sources 74 and 76 at the edges of right angle film 70. Light sources 74 and 76 are designed and positioned so as to emit substantially collimated beams of light in a direction almost parallel to planar surface 72 of right angle reflector film 70. The use of light sources on both sides of right angle reflector film 70 helps to provide uniform illumination over the entire area of display 68. Light sources 74 and 76 could be any type of lighting element. One possibility is the use of LEDs. LEDs are particularly advantageous for an application in which low power consumption is desired. An example of such an application is a display for a portable computer in which battery consumption is to be minimized.

Figure 7:
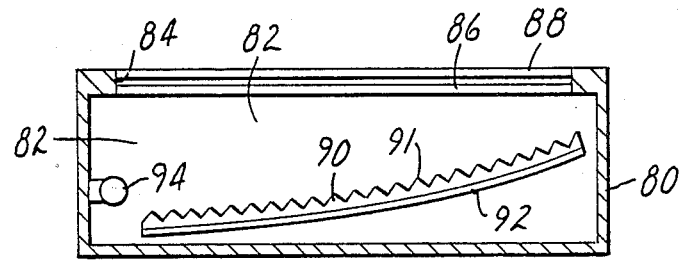
FIG. 7 is a schematic view of a second back-lit display according to the invention.

FIG. 7 illustrates another embodiment of the present invention. In FIG. 7 a housing 80 defines an optical cavity 82. Optical cavity 82 has an optical window 84. In optical window 84 are diffusing film 86 and display 88. Inside optical cavity 82 are right angle reflector film 90 having structured surface 91 and planar reflectorized surface 92. Also inside optical cavity 82 is light source 94 positioned at one edge of right angle reflector film 90. Light source 94 is arranged to direct light towards right angle reflector film 90 in a direction almost parallel to planar surface 92, so that partially collimated light will be directed through diffuser 86 and display 88. Right angle reflector film 90 is curved in order to produce a uniform illumination over the entire area of optical window 84.

The back-lit displays of FIG. 6 and FIG. 7 are advantageous over the prior art display of FIG. 5 in that they do not require the tapered diffuser of FIG. 5 and they produce uniform lighting without intentionally discarding any of the available light. Thus they may be more easily fabricated and will not waste energy by intentionally discarding light. Furthermore the displays of the invention may be made very thin, making them compact and allowing them to be light in weight.

Figure 8:
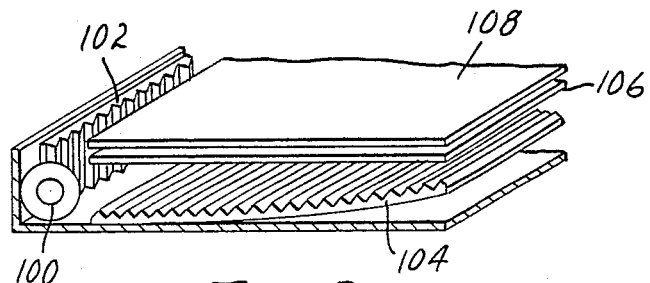
FIG. 8 is a schematic view of a third back-lit display according to the invention.

FIG. 8 of the present application shows another embodiment of the present invention. In the embodiment of FIG. 8 the light source includes light emitter 100 and right angle film 102. Light emitter 100 is preferably effectively a collimated point source. It may be, for example, an incandescent light with a collimating reflector, an LED or a laser. Light from light emitter 100 travels in a direction that is almost parallel to the smooth surface of right angle film 102.

The effect of right angle film 102 is to spread the light from light emitter 100 so the light source for right angle film 104 is a line source. The light leaves right angle film 102 in a direction almost parallel to the smooth surface of right angle film 104. After reflection by right angle film 104 it passes through diffuser 106 and display 108. By properly choosing the curvature of films 102 and 104 a uniform level of illumination may be achieved over all of display 108.

What is claimed is:

1. A back-lit display comprising:
    a housing defining an optical cavity having an optical window;
    a light reflecting film in said optical cavity, said light reflecting film having first and second major surfaces, said first surface being a structured surface having a plurality of triangular prisms thereon and said second surface being a smooth surface, and a light reflecting means adjacent said second surface for reflecting light approaching said second surface from said first surface;
    a first light source positioned so that light rays approach said film in a direction that is almost parallel to said second surface of said film; and
    display means in said optical window.

2. The back-lit display of claim 1 wherein said display means includes a liquid crystal display.

3. The back-lit display of claim 1 further comprising light diffusing means between said reflective film and said display means.

4. The back-lit display of claim 1 wherein said light source is positioned so that light rays approach said film in a direction that makes an angle of no more than 20° with said second surface.

5. The back-lit display of claim 1 further comprising a second light source positioned so that light rays approach said film in a direction that is almost parallel to said second surface of said film, said first and second light source being positioned adjacent opposite ends of said film.

6. The back-lit display of claim 5 wherein said display means includes a liquid crystal display.

7. The back-lit display of claim 5 further comprising light diffusing means between said reflective film and said display means.

8. The back-lit display of claim 5 wherein both of said light sources are positioned so that light rays approach said film in a direction that makes an angle of no more than 20° with said second surface.

9. The back-lit display of claim 8 wherein said display means includes a liquid crystal display.

10. The back-lit display of claim 9 further comprising light diffusing means between said reflective film and said display means.

11. The back-lit display of claim 1 wherein said light source is positioned adjacent one end of said film and said film curves so that said end of said film adjacent said light source is more distant from said display means than the opposite end of said film.

12. The back-lit display of claim 11 wherein said display means includes a liquid crystal display.

13. The back-lit display of claim 11 further comprising light diffusing means between said reflective film and said display means.

14. The back-lit display of claim 11 wherein said light source is positioned so that light rays approach said film in a direction that makes an angle of no more than 20° with said second surface.

15. The back-lit display of claim 14 wherein said display means includes a liquid crystal display.

16. The back-lit display of claim 15 further comprising light diffusing means between said reflective film and said display means.

17. The back-lit display of claim 1 wherein said light source comprises:
    a light reflecting film having first and second major surfaces, said first surface being a structured surface having a plurality of triangular prisms thereon and said second surface being a smooth surface and a light reflecting means adjacent said second surface for reflecting light approaching said second surface from said first surface; and
    a light emitting means positioned so that light rays approach said light source reflecting film in a direction that is almost parallel to said second surface of said light source reflecting film.

18. The back-lit display of claim 17 wherein said display means includes a liquid crystal display.

* * * * *